US012383612B2

(12) United States Patent
Witvliet et al.

(10) Patent No.: US 12,383,612 B2
(45) Date of Patent: Aug. 12, 2025

(54) VACCINE TO PROTECT A PIG AGAINST ACTINOBACILLUS PLEUROPNEUMONIAE

(71) Applicant: Intervet Inc., Madison, NJ (US)

(72) Inventors: Maarten Hendrik Witvliet, Oostrum (NL); Johanna Jacoba Elisabeth Bijlsma, Nijmegen (NL)

(73) Assignee: Intervet Inc., Rahway, NJ (US)

( * ) Notice: Subject to any disclaimer, the term of this patent is extended or adjusted under 35 U.S.C. 154(b) by 0 days.

(21) Appl. No.: 17/721,115

(22) Filed: Apr. 14, 2022

(65) Prior Publication Data

US 2022/0233675 A1 Jul. 28, 2022

Related U.S. Application Data

(62) Division of application No. 16/954,055, filed as application No. PCT/EP2018/085752 on Dec. 19, 2018, now abandoned.

(30) Foreign Application Priority Data

Dec. 20, 2017 (EP) .................................. 17209021

(51) Int. Cl.
A61K 39/102 (2006.01)
A61K 39/00 (2006.01)
C07K 14/285 (2006.01)

(52) U.S. Cl.
CPC .......... A61K 39/102 (2013.01); C07K 14/285 (2013.01); A61K 2039/54 (2013.01); A61K 2039/552 (2013.01); A61K 2039/55544 (2013.01)

(58) Field of Classification Search
None
See application file for complete search history.

(56) References Cited

U.S. PATENT DOCUMENTS

2004/0202678 A1  10/2004  Segers
2017/0340723 A1  11/2017  Witvliet et al.

FOREIGN PATENT DOCUMENTS

| CN | 102481350 A | 5/2012 |
| EP | 0595188 A2 | 5/1994 |
| EP | 0810283 A2 | 12/1997 |
| JP | 6135853 A | 5/1994 |
| WO | 9716532 A1 | 5/1997 |
| WO | 2011015614 A1 | 2/2011 |
| WO | 2016093157 A1 | 6/2016 |

OTHER PUBLICATIONS

Macjine Translation of WO 2016093157 A 1, pp. 1-8, 2016.*
Zheng et al. J. Biol. Chem. 285: 349-356, 2010.*
Sadilkova et al. Vet. Res. 43: 1-12, 2012.*
Ahrens, U. et al., Efficacy of the classical swine fever (CSF) marker vaccine Porcilis Pesti in pregnant sows, Veterinary Microbiology, 2000, pp. 83-97, vol. 77, No. 1-2.
Amar Safdar et al., Baculovirus-expressed influenza vaccine: a novel technology for safe and expeditious vaccine production for human use, Expert opinion on investigational drugs, Jul. 1, 2007, pp. 927-934, vol. 16, No. 7.
European Search Report for 17209021.9 dated Jun. 6, 2018, 13 pages.
Felberbaum, Rachael S., The baculovirus expression vector system: A commercial manufacturing platform for viral vaccines and gene therapy vectors, Biotechnology Journal, 2015, 702-714, 10.
Gomes, Amitha Reena et al., An Overview of Heterologous Expression Host Systems for the Production of Recombinant Proteins, Advances in Animal and Veterinary Sciences, 2016, 346-356, 4(7).
International Search Report for application PCTEP201808575 mailed on Mar. 25, 2019, 5 sheets.
Kim, Jung-Mi et al., Surface-Displayed Expression of a Neutralizing Epitope of ApxIIA Exotoxin in Saccharomyces cerevisiae and Oral Administration of It for Protective Immune Responses against Challenge by Actinobacillus bleuropneumoniae, Biosci. Biotech. Bioch., 2010, 1362-1367, 74.
Lui, J., et al., In vivo induced RTX toxin ApxIVA is essential for the full virulence of Actinobacillus pleuropneumoniae, Veterinary Microbiology, 2009, pp. 282-289, vol. 137, No. 3-4.
Mahendrasingh Ramjeet, et al., Mutation in the LPS outer core biosynthesis gene, galU, affects LPS Interaction with the RTX toxins ApxI and ApxII and cytolytic activity of Actinobacillus pleuropneumoniae serotype 1, Molecular Microbiology, 2008, pp. 221-235, vol. 70, No. 1.
Seah, J.N. et al., The N-Terminal Domain of RTX Toxin ApxI of Actinobacillus pleuropneumoniae Elicits Protective Immunity in Mice, Infection and Immunity, 2002, 6464-6467, 70(11).
Shin, Min-Kyoung et al., Oral immunization of mice with Saccharomyces cerevisiae expressing a neutralizing epitope of ApxIIA exotoxin from Actinobacillus pleuropneumoniae induces systemic and mucosal immune responses, Microbiology and Immunology, 2013, 417-425, 57.
Shin, Sung Jae et al., Enhancement of protective immune responses by oral vaccination with Saccharomyces cerevisiae expressing recombinant Actinobacillus pleuropneumoniae ApxIA or ApxIIA in mice, J. Vet. Sci., 2007, 383-392, 8(4).
Shin, Sung Jae et al., Induction of antigen-specific immune responses by oral vaccination with Saccharomyces cerevisiae expressing Actinobacillus pleuropneumoniae ApxIIA, FEMS Immunol. Med. Microbiol., 2005, 155-164, 43.

(Continued)

Primary Examiner — S. Devi
(74) Attorney, Agent, or Firm — Susanna C. Benn

(57) ABSTRACT

The present invention pertains to a vaccine to protect a pig against an infection with Actinobacillus pleuropneumoniae, the vaccine comprising an RTX toxin of Actinobacillus pleuropneumoniae recombinantly expressed by a baculovirus, and a pharmaceutically acceptable carrier.

6 Claims, No Drawings

(56) References Cited

OTHER PUBLICATIONS

Van Den Bosch, Han et al., Interference of outer membrane protein PalA with protective immunity against Actinobacillus pleuropneumoniae infections in vaccinated pigs, Vaccine, 2003, 3601-3607, 21.

Wang, C., et al., Positive role for rApxIVN in the immune protection of pigs against infection by Actinobacillus pleuropneumoniae, Vaccine, 2009, pp. 5816-5821, vol. 27, No. 42.

* cited by examiner

VACCINE TO PROTECT A PIG AGAINST *ACTINOBACILLUS PLEUROPNEUMONIAE*

CROSS-REFERENCE TO RELATED APPLICATIONS

This application is a divisional application of co-pending U.S. Ser. No. 16/954,055, filed on Jun. 16, 2020, which is a U.S. National Phase application under 35 U.S.C. § 371 of PCT/EP2018/085752, filed on Dec. 19, 2018, which claims priority to EP Application Serial No. 17209021.9, filed on Dec. 20, 2017. The contents of all of which are hereby incorporated by reference in their entireties.

GENERAL FIELD OF THE INVENTION

The invention in general pertains to a vaccine for protecting a pig against an infection with *Actinobacillus pleuropneumoniae*.

BACKGROUND OF THE INVENTION

The present invention pertains to a vaccine directed against porcine pleuropneumonia, a world-wide disease causing substantial economic loss to the swine industry. The etiological agent of porcine pleuropneumonia is *Actinobacillus pleuropneumoniae* (APP), a gram-negative bacterium belonging to the family Pasteurellaceae. The disease is transmitted by the aerosol route or direct contact with an infected pig, and is characterized by hemorrhagic, fibrinous and necrotic lung lesions. The clinical picture may range from peracute to chronic and asymptomatic carrier pigs can transmit the disease when introduced into uninfected herds. Based on capsular polysaccharides and lipopolysaccharide (LPS) O-chain components, 15 serovars have been described. Serotyping and other genetic typing methods for *Actinobacillus pleuropneumoniae* have contributed greatly to surveillance and epidemiological studies. These tools provide important information for decision making in control programs aimed at eradication of virulent types of the bacterium. In North America, serovars 1, 5 and 7 are reported to be the most prevalent, while serovars 2 and 9 are most commonly isolated in Europe, and serovar 15 is the predominant isolate from Australian pigs.

The virulence factors described for *Actinobacillus pleuropneumoniae* include LPS, capsular polysaccharides, Apx toxins I-IV (so called repeats-in-toxins or RTX toxins, outer membrane proteins (OMPs) and various iron acquisition systems. The RTX toxins of *Actinobacillus pleuropneumoniae* (the Apx toxins I, II and III) have been described by Frey in *Trends in Microbiology* 257, Vol. 3, No. 7, July 1995). Later, a fourth RTX toxin of APP (called Apx IV) was found (see Dreyfus et al. in *Veterinary Microbiology*, 2004 Apr. 19; 99 (3-4): 227-238). However, the overall contribution of each component to the infection process remains unclear, as do the mechanisms of pathogenesis of this bacterium. Almost all of the currently available vaccines against *A. pleuropneumoniae* are either inactivated whole-cell bacterins or subunit combinations of Apx toxins and proteins, optionally in combination with outer membrane fractions. In any case, it has become commonly understood that for obtaining adequate protection lipopolysaccharide (LPS) has to be present in a vaccine (Julien Gouré et al. in *BMC Genomics* 2009, 10:88, published 24 Feb. 2009; Dubreuil et al. in *Animal Health Research Reviews* 1(2): 73-93, 2000 December). Indeed, it is known that the specific binding between LPS and the Apx toxins plays a major role in the improved immunogenicity of the toxins (see i.a. Ramjeet et al. in *Molecular Biology*, 2008, 70(1), pp 221-235) which may explain the adequate protection of a combination sub-unit vaccine wherein the Apx toxin is present in a complex with LPS.

A serious disadvantage of lipopolysaccharide is its endotoxic nature, thus being associated with multiple unwanted side effects such as lethargy, diarrhoea, vomiting, loss of appetite or even death. At first glance it is therefore tempting to lower the amount of LPS in a vaccine or to detoxify the LPS. However, an adequate APP vaccine depends on the presence of LPS and thus, as is commonly known, lowering the amount of LPS inherently decreases the efficacy of the vaccine. In the alternative, the negative impact of LPS may be negated by adding the antibiotic polymyxin to the vaccine as is known from WO2011/015614. However, from a regulatory point of view, adding an antibiotic to a vaccine is severely restricted. This solution can therefore not be used in all regulatory jurisdictions.

Indeed, it is the current understanding that to arrive at such a high level of protection, at least one Apx toxin needs to be present in a vaccine, the toxin being present in an immunological complex with a hetero molecule such as LPS. Although it is known that purified Apx toxins may provide some level of protection (see i.a. Bhatia et al in *Veterinary Microbiology*, 29, 1991, 147-158), for obtaining adequate protection, using a purified Apx toxin as an antigen in a vaccine is understood not to be sufficient. Many examples are known of Apx toxin expressed in the gram-negative bacterium *E. coli*. Although sometimes referring to "purified" recombinant Apx toxin when produced by *E. coli*, in each of these cases the toxin is complexed with LPS as a result of contact with LPS as contained in the bacterial cell wall of *E. coli*. More exotic expressions systems for truly obtaining purified Apx toxin, not complexed with LPS or another hetero toxin are also known in the art. Kyung-Yeol Lee et al. describe in *FEMS Immunol Med Microbiol* 48, 2006, 381-389 the induction of a protective immune response against an infection with *Actinobacillus pleuropneumoniae* with a recombinant Apx toxin produced in a transgenic tobacco plant. However, no protection in pigs was shown. Also the vaccine needed to be administered in four consecutive doses, given orally. For the practice of vaccinating pigs this is not a realistic option. Correspondingly, Mi-Young Kim et al. did show in *Protein Expression and Purification* 132, 2017, 116-123, that Apx toxin could be expressed in transgenic rice callus, and that the purified toxin, when administered intranasally could provide at least some protection against an infection with *Actinobacillus pleuropneumoniae* in mice. However, protection in pigs was not shown, let alone protection at a level comparable with commercially available vaccines to protect against APP.

OBJECT OF THE INVENTION

It is an object of the invention to provide an alternative vaccine to adequately protect piglets against an infection with *Actinobacillus pleuropneumoniae*, preferably at a level comparable with protection arrived at when using a commercially available APP vaccine.

SUMMARY OF THE INVENTION

In order to meet the object of the invention a vaccine to protect a pig against an infection with *Actinobacillus pleuropneumoniae* has been devised, the vaccine comprising an RTX toxin of *Actinobacillus pleuropneumoniae* recombinantly expressed by a baculovirus, and a pharmaceutically acceptable carrier.

Surprisingly the current vaccine, comprising an isolated toxin without LPS or another hetero toxin being present, may lead to adequate protection, even at a level comparable with the protection obtainable when using a vaccine such as PORCILIS® APP (MSD Animal Health, Boxmeer, The Netherlands). Although baculovirus expression as such is commonly known and has been used since many years to express immunogens of either viral or bacterial pathogens, it has not been used to provide an adequate vaccine against APP by expressing one or more RTX toxcins. Baculoviruses are DNA viruses capable of infecting more than 600 insect species. The most commonly employed baculovirus in biotechnology is *Autographa californica*. Baculovirus possesses a circular double-stranded DNA (about 134 kb), which is packed within a rod-shaped nucleocapsid and enveloped by a membrane derived from host cells. After infection of insects, baculovirus can be released from the cells in a budded form or be embedded within a polyhedron consisting of virus-expressed polyhedrin and p10 proteins. The polyhedrin and p10 proteins are abundantly expressed but are dispensable for baculovirus replication, thus heterologous genes can be cloned under the control of polyhydrin or p10 promoter to generate the recombinant baculovirus. The resultant recombinant baculovirus can be used to infect cultured insect cells for robust protein expression, as known since the 1980's. To date, various commercial baculovirus vector systems have been developed (e.g., BAC-TO-BAC™, INVITROGEN: BACULODIRECT™, INVITROGEN: PROEASY™, AB VECTOR), allowing for gene cloning and recombinant baculovirus construction in a 'plug and play' fashion (see for example Lin S Y, Chen G Y, Hu Y C. *Recent Pat Biotehnol* 2011:5:1-11). Furthermore, a number of engineered baculovirus vectors such as FLASHBAC™ and FLASHBACGOLD™ (Oxford Expression Technologies Ltd) have been developed to improve the recombinant protein expression by deleting certain viral genes (e.g., chiA and v-cath) in the baculovirus genome (for example see Hitchman R B, Possee R D, King L A. *Recent Pat Biotechnol* 2009:3:46-54). In addition, MULTIBAC™ system (Geneva Biotech) allows for rapid and flexible construction of baculovirus with multiple gene expression cassettes by homing endonuclease and Cre-loxP transposition. Conversely, SWEETBAC™ system based on MULTIBAC™ is developed to overcome the glycosylation problems in insect cells and express mammalianized proteins (for example see Palmberger D, Klausberger M, Berger I, et al. *Bioengineered* 2013:4:78-83).

The invention has also led to an RTX toxin of *Actinobacillus pleuropneumoniae* recombinantly expressed by a baculovirus for use in a method to protect a pig against an infection with *Actinobacillus pleuropneumoniae* by administering a vaccine comprising the RTX toxin and a pharmaceutically acceptable carrier to the animal.

Next to this, the invention enables the use of an RTX toxin of *Actinobacillus pleuropneumoniae* recombinantly expressed by a baculovirus for manufacturing a vaccine to protect a pig against an infection with *Actinobacillus pleuropneumoniae*, by mixing the RTX toxin with a pharmaceutically acceptable carrier, and a method of protecting a pig against an infection with *Actinobacillus pleuropneumoniae*, by administering a vaccine comprising an RTX toxin of *Actinobacillus pleuropneumoniae* recombinantly expressed by a baculovirus and a pharmaceutically acceptable carrier, to the pig.

Definitions

A vaccine is a pharmaceutical composition that is safe to administer to a subject animal, and is able to induce protective immunity in that animal against a pathogenic microorganism, i.e. to induce a successful protection against an infection with the micro-organism. In general, a vaccine can be formulated by using art-known methods that basically comprise admixing one or more antigens (live or inactivated, whole cell, extract, purified fraction or subunit) with a pharmaceutically acceptable carrier, e.g. a liquid carrier such as (optionally buffered) water or a solid carrier such as commonly used to obtain freeze-dried vaccines. Optionally, other substances such as adjuvants, stabilisers, viscosity modifiers or other components are added depending on the intended use or required properties of the vaccine.

A pharmaceutically acceptable carrier is a biocompatible medium, viz. a medium that after administration does not induce significant adverse reactions in the subject animal, capable of presenting the antigen to the immune system of the host animal after administration of the vaccine. Such a pharmaceutically acceptable carrier may for example be a liquid containing water and/or any other biocompatible solvent or a solid carrier such as commonly used to obtain freeze-dried vaccines (based on sugars and/or proteins), optionally comprising immunostimulating agents (adjuvants). Optionally other substances such as stabilisers, viscosity modifiers or other components are added depending on the intended use or required properties of the corresponding vaccine.

Protection against an infection with a micro-organism is aiding in preventing, ameliorating or curing an infection with that micro-organism or a disorder arising from that infection, for example to prevent or reduce one or more clinical signs resulting from the infection with the pathogen.

Systemic administration of a vaccine means that the vaccine reaches the circulatory system of the body, i.e. the system comprising the cardiovascular and lymphatic system, thus affecting the body as a whole rather than a specific locus such as the gastro-intestinal tract. Systemic administration can be performed e.g. by administering the vaccine into muscle tissue (intramuscular), into the dermis (intradermal), underneath the skin (subcutaneous), underneath certain mucosa (submucosal), in the veins (intravenous) etc.

The RTX toxins of *Actinobacillus pleurpneumoniae* (the Apx toxins) are the protein toxins as produced by *Actinobacillus pleurpneumoniae* that contribute significantly to the pathogenesis of porcine pleuropneumonia. ApxI (about 105 kDa) is strongly hemolytic and cytotoxic to leukocytes and is encoded by the apxIA gene (1023 codons) that is part of the apxI-CABD operon. ApxII (about 105 kDa) is weakly hemolytic and moderately cytotoxic. The apxII operon contains the structural gene apxIIA (956 codons) and the apxIIC gene. ApxIII (about 120 kDa), encoded by the apxIIIA gene (1052 codons), is nonhemolytic but strongly cytotoxic toward porcine lung macrophage. ApxIV, is encoded by the apxIVA gene, which varies in length from about 1382 to about 1805 codons in different serotypes. ApxIV presents significant sequence similarity with the iron-regulated RTX proteins of *Neisseria meningitidis*, FrpA and FrpC. As is commonly known, recombinant expression of an RTX toxin of APP may lead to a protein that is only a fraction of the naturally occurring Appx toxin (leaving out parts that are not essential for obtaining an adequate immune response) and having a sequence identity in the overlapping region that is less than 100% with the naturally occurring toxin, preferably having an identity of more than 70, 75, 80, 81, 82, 83, 84, 85, 86, 87, 88, 89, 90, 91, 92, 93, 94, 95, 96, 97, 98, 99, up to 100% with any of the naturally occurring ApxI, ApxII, ApxIII or ApxIV. Sequence identity may be established using the BLAST program using the blastp algorithm with default parameters. Typically an immunogenic fraction of an Apx has a length of at least about 35% of the full length protein (see Infection and Immunity, Vol. 70, No. 11, November 2002, p 6464-6467) e.g. 35, 40, 45, 50, 55, 60, 65, 70, 75, 80, 85, 90, 95 up to 100%, but even fractions significantly smaller than 35% have been shown to be potentially effective as immunogens (see Vaccine, 17 (1999), 441-447).

EMBODIMENTS OF THE INVENTION

In a first embodiment, the vaccine comprises the RTX toxin ApxI. ApxI is produced by many APP serovars and by having only this toxin in the vaccine, broad protection can thus be obtained.

In another embodiment, the vaccine is administered systemically, for example by intramuscular or intradermal administration.

The invention will now be further explained using the following non-limiting examples.

EXAMPLES

Example 1: Recombinant Expression of ApxI

Construction of Transfervector pFastbac-ApxIA

The rApxIA gene was synthesized based on the ApxIA amino acid sequence of the *Actinobacillus pleuropneumoniae* strain 4074, Swiss prot accession number: P55128. The gene was codon optimized for baculovirus polyhedrin usage and a Kozak sequence (TATAAAT) and a 3' hexahistidine tag were included. The rApxIA-His gene was cloned behind the polyhedrin promoter of plasmid pFastbac1 (Life Technologies, Carlsbad, USA) as a BamHI fragment, resulting in plasmid pFastbac-ApxIA TAT.

Generation of Recombinant Baculovirus BacdCCApxIA-TAT.

Recombinant baculovirus was generated using the plasmid as described here above in the Bac to Bac system (Life Technologies, Carlsbad, USA) according to manufacturer's protocol. *E. coli* cells used for transformation contained the parental baculovirus with a deletion of the chitinase and v-cathapsin genes (Kaba S A, Salcedo A M, Wafula P O, Vlak J M, van Oers M M. *J Virol Methods*. 2004 Dec. 1: 122(1): 113-8.) *E. coli* bacteria were grown in an animal component free (ACF) medium.

BacdCCApxIA-TAT DNA was isolated from *E. coli* and used for transfection into *Spodoptera frugiperda* (Sf)9-900 cells. Sf9-900 cells were grown in an animal compound free medium. Expression of the 110 kDa ApxIA protein was confirmed using SDS-PAGE gels, Western blots and Immune Fluorescence Assays using an anti-histidine-tag monoclonal antibody. Transfection supernatants were once amplified and the resulting virus stock was used for all further virus cultures.

Histag Purification Baculovirus Produced ApxIA.

Sf9-900 cells were infected with the BacdCCApxIA-TAT baculovirus with a multiplicity of infection of 0.1, followed by culturing for 4 to 5 days at 27.5° C. From those cells rApxIA-His protein was purified using the AKTA Avant protein purification system (GE Healthcare Life Sciences, Cleveland, USA) using a HIStrap FF column. Lysates were made from insect cells infected with BacdCCApxIA-TAT using Lysis buffer TRITON X114 (0.15 M NaCl, 10 mM Tris-HCl pH8, 2.5 mM CaCl2, 1 mM DTT, 1% TRITON X114). After centrifugation the pellet was resuspended in wash buffer (50 mM Tris pH=8, 300 mM NaCl, 6 M Ureum, 2.5 mM CaCl2, 1 mM DTT) and filtered using a 0.45 μM filter before applying to the AKTA Avant. After equilibration of the column with denaturing wash buffer the sample was applied twice to the column at a rate of 3 ml/min. Protein bound to the column was renatured with redox buffer (50 mM Tris pH=8, 300 mM NaCl, 2.5 mM CaCl2, 0.1% oxidized glutathione, 0.01% reduced glutathione, 1 mM DTT) and eluted from the column with a linear imidazole gradient, using elution buffer (50 mM Tis pH=8, 300 mM NaCl, 2.5 mM CaCl2, 1 mM DTT, 500 mM Imidazole). Purified ApxI protein was dialyzed against dialysis buffer (50 mM Tris pH=8, 300 mM NaCl, 2.5 mM CaCl2) using Slide-A-Lyzer Dialysis Cassettes (Thermo Scientific, Waltham, USA) with several buffer changes.

Example 2: Vaccine Efficacy

Vaccine Formulation

Two different vaccines were made for the study. A first vaccine comprised purified baculovirus expressed ApxI as obtained with a method described under Example 1. A second vaccine for use as a positive control was comparable with the commercially available vaccine PORCILIS® APP, comprising ApxI and ApxII purified from the culture supernatant of *A. pleuropneumoniae* (and thus complexed with LPS), also denoted as "native ApxI+ApxII". The study vaccine different from the commercially available vaccine PORCILIS® APP in that it did not contain the ApxIII toxin. However, for the challenge with a serotype 10 field isolate, this is not relevant (serotype 10 does not produce ApxIII). The antigens were mixed with a mineral oil-containing adjuvant (XSolve, available from MSD Animal Health, Boxmeer, The Netherlands) at a final concentration of 25 μg/ml for each antigen.

Vaccination Protocol

Three groups of eight piglets from an *A. pleuropneumoniae* free herd were used. The two vaccines were administered intramuscularly as a 2 ml dose at five and nine weeks of age. The remaining eight piglets were injected with PBS and used as non-vaccinated negative control group. At regular intervals, blood samples were taken for serology.

*A. pleuropneumoniae* Serotype 10 Challenge Infection

At approximately 12 weeks of age, all 24 piglets received a challenge infection. The challenge compound was a serotype 10 field isolate (strain HV211) of *A. pleuropneumoniae*. The challenge culture was freshly prepared prior to challenge. The piglets were challenged with *A. pleuropneumoniae* by the aerosol route. The aerosol was given by means of a Devilbis Nebulizer (total amount 30 ml). The challenge dose was determined by plate counting and the suspension was found to contain $7.0 \times 10^8$ CFU/ml.

After challenge, respiratory disease and other abnormalities were scored daily for a period of seven days, after which the surviving animals were necropsied.

The scoring system used was as follows:

0 = normal
1 = shivering
2 = depressed
3 = increased respiration rate
4 = vomiting
5 = diarrhoea 6 = coughing
7 = abdominal respiration
8 = dyspnoea For animal welfare reasons, animals that were found to be moribund were euthanized. Pigs that were found dead or had been euthanized were inspected for typical *Actinobacillus pleuropneumoniae* lesions, of which the extent per lung lobe was scored on a 0-5 scale (max score per animal: 35). Also, the lungs of the surviving animals were scored at day seven post challenge.

Results

All pigs were serologically negative at the start of the experiment, and at the time of challenge the vaccinated animals had seroconverted for ApxI, as measured by ELISA with native ApxI as the coating antigen. The main antibody titres were $\log_2$ 12.9±1.6 and 13.1±1.1 for the Baculo-ApxI and native ApxI+ApxII groups, respectively. Table 1 provides a summary of the challenge results, and Table 2 shows the clinical abnormalities observed for the individual pigs.

TABLE 1

Protection of the piglets

| Vaccine | Mortality [n/n$_{tot}$] | Mean lung lesion score |
|---|---|---|
| Baculo-ApxI | 2/8* | 1.5 ± 3.1* |
| Native ApxI + ApxII | 1/8* | 0.4 ± 1.1* |
| PBS | 8/8 | 20.3 ± 5.7 |

*significantly different from controls (p < 0.05, Fischer's exact-test for mortality rate and Mann-Whitney U-test for lesion scores)

TABLE 2

Clinical abnormalities per group

| | Baculo-ApxI | | Native ApxI + ApxII | | PBS | |
|---|---|---|---|---|---|---|
| pig | Abnorm[1] | Dead day[2] | Abnorm[1] | Dead day[2] | Abnorm[1] | Dead day[2] |
| 1 | 2 | — | 2 | — | 2, 3, 7, 8 | 1 |
| 2 | 2, 7 | 3 | 2, 3, 7 | 1 | 2, 3, 7, 8 | 1 |
| 3 | 0 | — | 0 | — | 2, 3, 7, 8 | 1 |
| 4 | 2, 5 | — | 0 | — | 2, 3, 7, 8 | 1 |
| 5 | 0 | — | 0 | — | 2, 3, 7, 8 | 1 |
| 6 | 2, 3, 7 | 3 | 0 | — | 2, 3, 7, 8 | 1 |
| 7 | 0 | — | 2, 7 | — | 2, 3, 7, 8 | 1 |
| 8 | 0 | — | 0 | — | 2, 3, 7, 8 | 1 |

[1]Clinical abnormalities observed (scored as described under challenge infection)
[2]Died/euthanized on indicated day post challenge Significant reductions of clinical signs, mortality and lung lesion were observed for both vaccinated groups. The difference between the two vaccine groups was not statistically significant. It can therefore be concluded that the vaccine containing RTX toxin recombinantly expressed by baculovirus provides protection that is similar to the protection provided the commercial vaccine PORCILIS® APP.

The invention claimed is:

1. A method of protecting a pig against an infection with *Actinobacillus pleuropneumoniae* by administering to the pig a dose of a vaccine, wherein the vaccine comprises an isolated and purified 110 kDa ApxI toxin of *Actinobacillus pleuropneumoniae* expressed recombinantly by a baculovirus, wherein the vaccine is without LPS or another heterotoxin, and wherein the vaccine further comprises an adjuvant.

2. The method of claim 1, wherein the vaccine is administered systemically.

3. The method of claim 1, wherein the vaccine is administered intramuscularly.

4. The method of claim 1, wherein the vaccine is administered intradermally.

5. The method of claim 1, wherein the vaccine further comprises a pharmaceutically acceptable carrier.

6. The method of claim 1, wherein the adjuvant is a mineral oil-containing adjuvant.

* * * * *